(12) United States Patent
Goodman

(10) Patent No.: US 11,684,924 B2
(45) Date of Patent: Jun. 27, 2023

(54) SPECIMEN COLLECTION DEVICE

(71) Applicant: HURONMED, LLC, Ann Arbor, MI (US)

(72) Inventor: John F. Goodman, Ann Arbor, MI (US)

(73) Assignee: HURONMED, LLC, Ann Arbor, MI (US)

( * ) Notice: Subject to any disclaimer, the term of this patent is extended or adjusted under 35 U.S.C. 154(b) by 650 days.

(21) Appl. No.: 16/711,887

(22) Filed: Dec. 12, 2019

(65) Prior Publication Data

US 2020/0188921 A1 Jun. 18, 2020

Related U.S. Application Data

(60) Provisional application No. 62/781,015, filed on Dec. 18, 2018.

(51) Int. Cl.
| | |
|---|---|
| *B01L 3/00* | (2006.01) |
| *G01N 1/14* | (2006.01) |
| *A61B 10/02* | (2006.01) |
| *A61B 17/00* | (2006.01) |
| *A61B 10/00* | (2006.01) |
| *A61B 10/04* | (2006.01) |
| *G01N 1/00* | (2006.01) |

(52) U.S. Cl.
CPC ............ *B01L 3/54* (2013.01); *A61B 10/0045* (2013.01); *A61B 10/0283* (2013.01); *A61B 10/04* (2013.01); *A61B 17/00234* (2013.01); *G01N 1/14* (2013.01); *A61B 2010/0225* (2013.01); *A61B 2017/00238* (2013.01); *G01N 2001/002* (2013.01)

(58) Field of Classification Search
None
See application file for complete search history.

(56) References Cited

U.S. PATENT DOCUMENTS

| | | | |
|---|---|---|---|
| 3,788,484 A | 1/1974 | Godin | |
| 4,376,053 A | 3/1983 | Bullock | |
| 5,347,991 A * | 9/1994 | Nakao | A61M 1/0001 |
| | | | 600/156 |
| 5,348,542 A | 9/1994 | Ellis | |
| 5,380,665 A | 1/1995 | Cusack et al. | |
| 6,299,763 B1 * | 10/2001 | Ashman | B01D 35/02 |
| | | | 210/450 |
| 6,505,356 B1 | 1/2003 | Leonard et al. | |
| 8,562,542 B2 * | 10/2013 | Binette | A61B 10/0096 |
| | | | 600/562 |
| 9,671,318 B1 * | 6/2017 | Bedoe | A61B 10/02 |

(Continued)

OTHER PUBLICATIONS

International Search Report dated Feb. 27, 2020 in connection with International Application No. PCT/US19/66469.

*Primary Examiner* — Benjamin S Melhus
(74) *Attorney, Agent, or Firm* — Behmke Innovation Group LLC; Kenneth J. Heywood; James E. Denker

(57) ABSTRACT

A specimen collection device and a method of using the specimen collection device are disclosed herein. In some aspects, the specimen collection device allows for the individual collection of specimens via a removable specimen tray that can easily be swapped during a procedure. The specimen collection device includes a flexible sealing element for the continual use of suction during the procedure even when the specimen tray is not inserted.

13 Claims, 26 Drawing Sheets

(56) References Cited

U.S. PATENT DOCUMENTS

| | | | |
|---|---|---|---|
| 11,273,393 B2* | 3/2022 | Mir | B01D 29/01 |
| 11,278,184 B2* | 3/2022 | Johnsen | A61B 1/00068 |
| 2003/0214312 A1 | 11/2003 | Khatchatrian et al. | |
| 2007/0191731 A1* | 8/2007 | Kaye | A61B 10/0283 |
| | | | 600/565 |
| 2008/0200837 A1 | 8/2008 | Frazier et al. | |
| 2009/0234192 A1* | 9/2009 | Okada | A61B 10/0096 |
| | | | 600/156 |
| 2012/0095369 A1* | 4/2012 | Teixeira | A61B 1/2676 |
| | | | 600/573 |
| 2015/0359949 A1* | 12/2015 | Yeager | A61M 1/79 |
| | | | 435/283.1 |
| 2017/0160169 A1* | 6/2017 | Bedoe | A61B 10/02 |
| 2019/0054217 A1* | 2/2019 | Axon | A61B 10/0283 |
| 2019/0343493 A1* | 11/2019 | McCabe | A61M 1/0001 |
| 2021/0162101 A1* | 6/2021 | Zollinger | A61B 10/0283 |

* cited by examiner

SPECIMEN COLLECTION DEVICE

CROSS-REFERENCE TO RELATED APPLICATION

This application claims the benefit of U.S. Provisional Application No. 62/781,015, entitled SPECIMEN COLLECTION DEVICE, by Goodman, filed Dec. 18, 2018, which is incorporated herein by reference.

TECHNICAL FIELD

The present disclosure relates generally to medical devices and, more particularly, to a specimen collection device for use during endoscopic and other medical procedures.

BACKGROUND

Endoscopic procedures are routinely performed to explore a patient's cavities and organs, to search for suspicious structures, such as polyps, that may indicate the presence of cancer or other diseases. In cases when a suspicious structure is detected, a biopsy is typically performed, to retrieve a specimen for post-procedural analysis.

Endoscopic systems used for such procedures are configured with a mechanism that provides lavage to the viewing site, to clear away residual body waste or blood that might otherwise obstruct the field of view of the clinician. These endoscopic systems are furthermore configured with vacuum systems, to aspirate the lavage fluid from the viewing site. The vacuum systems are also used to aspirate biopsied samples that have been excised. Suction canisters are typically situated between the vacuum source and the endoscope, to collect aspirated body waste and lavage fluid to minimize contamination of the vacuum source. Likewise, the suction canister can be used to capture aspirated biopsies. In the latter case, specimens must be removed from the canister and placed into a small jar of formalin for preservation until they can be histologically analyzed.

It is important to remove samples, as they are collected, to ensure proper identification of the location and extent of disease. This can be a particularly cumbersome and relatively time-consuming task, as the aspirated sample may be comingled with bodily waste and fluids. Medical staff must first separate the specimen from this waste, a task typically performed by disassembling the canister and pouring the contents over gauze. The specimen can then be picked off the gauze and placed into the formalin vial. The canister must be then reassembled to prepare for the next specimen. During this time, the vacuum system is unavailable for use, potentially delaying the procedure.

BRIEF DESCRIPTION OF THE DRAWINGS

The embodiments herein may be better understood by referring to the following description in conjunction with the accompanying drawings in which like reference numerals indicate identically or functionally similar elements, of which.

Figure 1:
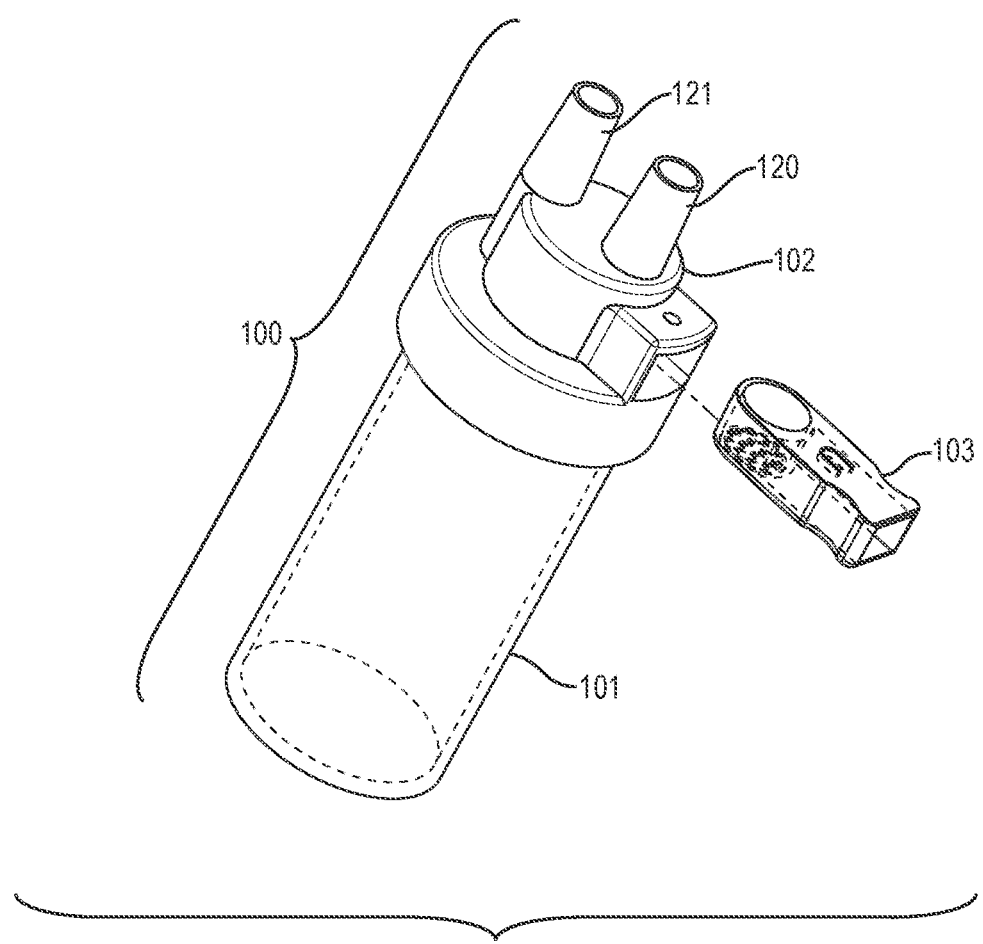
FIG. 1 is an isometric view of a specimen collection device with integrated suction canister and associated sieve, according to various embodiments.

In the figures, reference numbers refer to the same or equivalent parts of the present invention throughout the several figures of the drawing.

SUMMARY

According to various embodiments described herein, a specimen collection device is disclosed. The specimen collection device includes an inlet port and an outlet port on opposing ends of the specimen collection device. The inlet and outlet ports define an aperture that extends through the specimen collection device. The specimen collection device includes an access port located substantially perpendicular to the aperture defined by the inlet and outlet ports and configured to receive a specimen tray having an outlet sieve such that the outlet sieve of the specimen tray is aligned with the aperture when the specimen tray is fully inserted into the access port. The specimen collection device further includes a flexible sealing element of a substantially curved shape that is located at a first position within the specimen collection device between the aperture and the access port such that the access port is sealed when the specimen tray is not inserted into the access port, deforms in response to an insertion force applied to the specimen tray to insert the specimen tray into the access port, and is located at a second position that is on an opposing side of the aperture as that of the first position when the specimen tray is fully inserted into the access port. In some embodiments, the specimen tray includes tactile grips to facilitate retrieval of the specimen tray.

In some embodiments, the specimen collection device may further include a specimen tray, wherein the outlet sieve of the specimen tray is disposed within a sample cavity located at an end of the specimen tray. The specimen collection device may also include a suction port. The specimen collection device, in some embodiments, includes a suction canister. In a further embodiment, the specimen collection device includes one or more protrusions that directly couple the specimen collection device to the suction canister. In another embodiment, the specimen collection device includes a tube coupled to the suction canister and to the outlet port of the specimen collection device. In another embodiment, the suction canister includes a first port to receive the tube for coupling the suction canister to the outlet port of the specimen collection device and a suction port. In a further embodiment, the specimen collection device is configured to couple with an endoscope.

In another embodiment, the flexible sealing element is of a cylindrical shape when the flexible sealing element is located within the specimen collection device at the first position. The specimen collection device may include a sealing element retaining wall that provides a force to the flexible sealing element that is opposite that of the insertion force when the specimen tray is inserted into the access port, thereby causing the flexible sealing element to deform when the specimen tray is inserted into the access port. In some embodiments, the flexible sealing element is arc-shaped when located in the first position and contacts the sealing element retaining wall at one or more locations along the sealing element retaining wall.

In an additional embodiment, a method of using a specimen collection device is disclosed herein. The method includes applying suction to an aperture defined by the specimen collection device that extends from an inlet port of the specimen collection device to an outlet port of the specimen collection device, inserting a specimen tray into an access port of the specimen collection device to deform a flexible sealing element of the collection device, receiving one or more specimens in the specimen tray, and withdrawing the specimen tray to return the flexible sealing element to an original position. Withdrawing the specimen tray may further include sealing off the access port of the specimen collection device with the flexible sealing element.

The method may further include transferring the specimen tray direction into a container for assessment. The method may also include coupling the specimen collection device to an endoscope. In another embodiment, the method may include the flexible sealing element is deformed by moving from a first position within the specimen collection device between the aperture and the access port to a second position that is on an opposing side of the aperture as that of the first position when the specimen tray is fully inserted into the access port.

The method may also include, wherein receiving one or more specimens in the specimen tray, filtering a substance containing one or more specimens through an outlet sieve disposed within a sample cavity located at an end of the specimen tray; and retaining the one or more specimens within the sample cavity.

In another embodiment, the specimen collection device may include means for directing suction through the specimen collection device, collection means for collecting a specimen within a pathway of the suction, access means for accepting the collection means into the specimen collection device, and sealing means for sealing the access means when the collection means is not inserted into the access means. In a further embodiment, the second collection means for collecting specimens when the first collection means is not inserted into the access means of the specimen collection device.

DETAILED DESCRIPTION

In the following description, the term "distal" will refer to a position on the device closer to the patient. The term "proximal" will refer to a position on the device farther from the patient.

Referring now to the drawings above, FIG. 1 illustrates a specimen collection device 100, in accordance with various embodiments herein. As shown, specimen collection device 100 includes a suction canister 101, a suction canister lid 102, a specimen tray 103, an inlet port 120, and a suction port 121. The suction port 121 may receive a tube for coupling the suction canister 101 to an outlet port of the specimen collection device 100. In some embodiments, the specimen collection device 100 is configured to couple with an endoscope.

Figure 2:
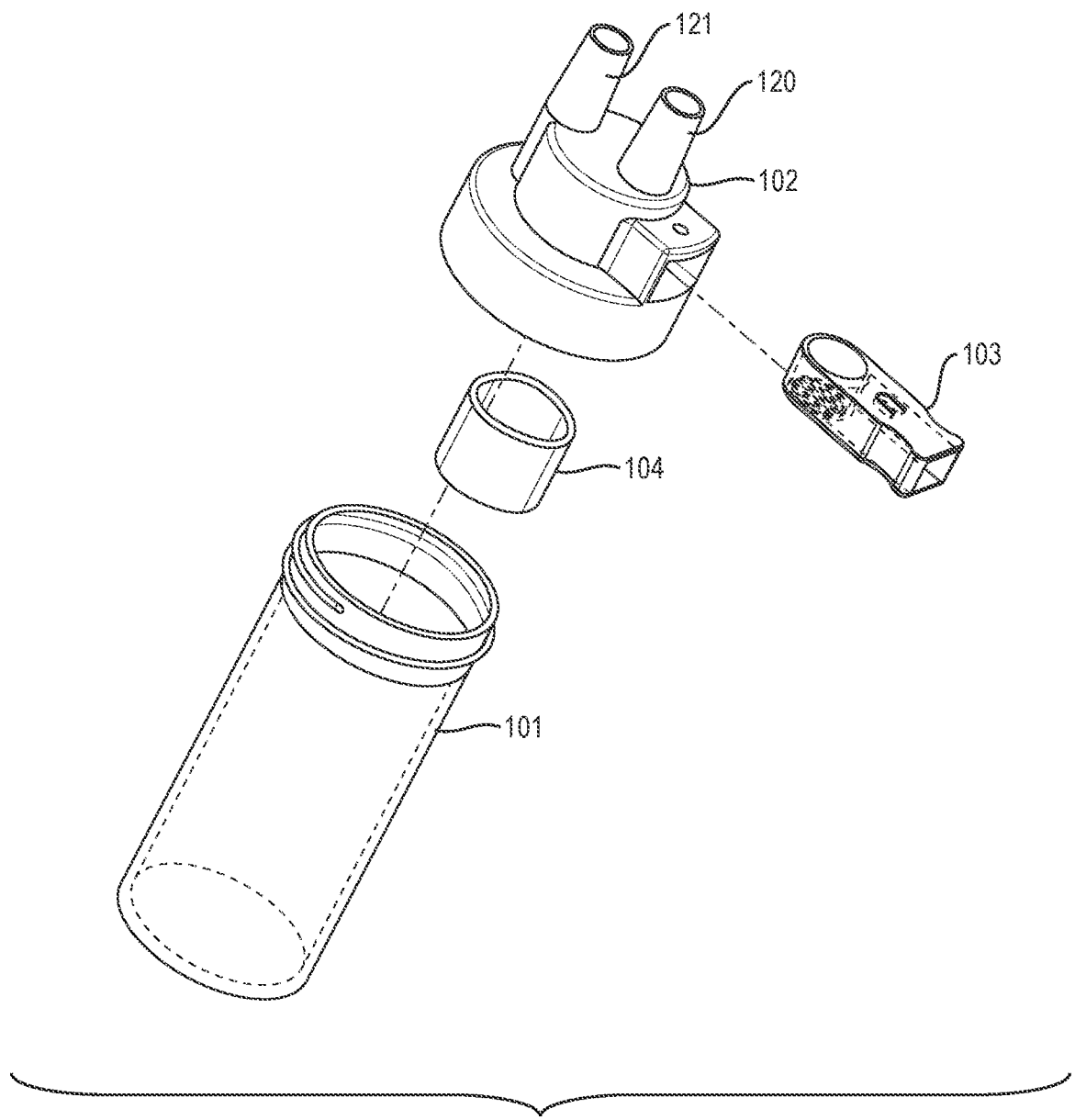
FIG. 2 is an exploded view of the specimen collection device, according to various embodiments.
Figure 3:
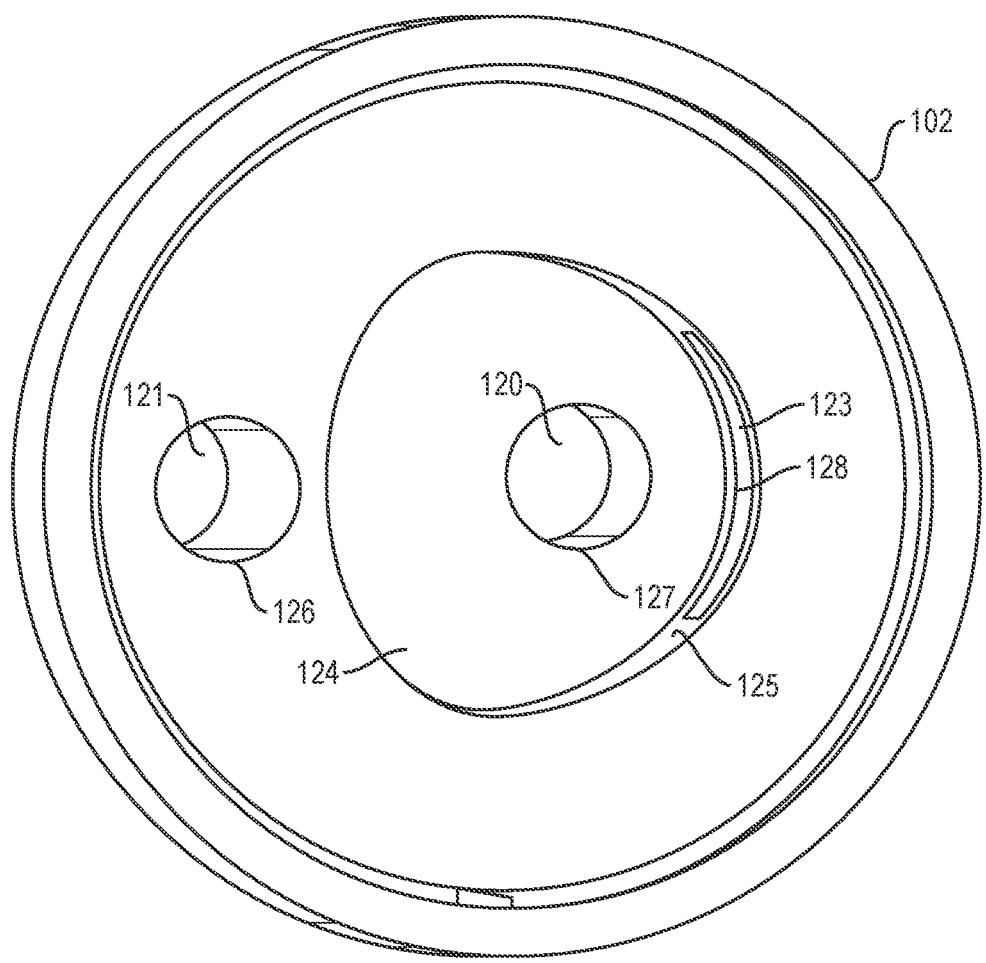
FIG. 3 is a bottom view of the cap of the integrated suction canister of the specimen collection device shown without sealing element, according to various embodiments.
Figure 4:
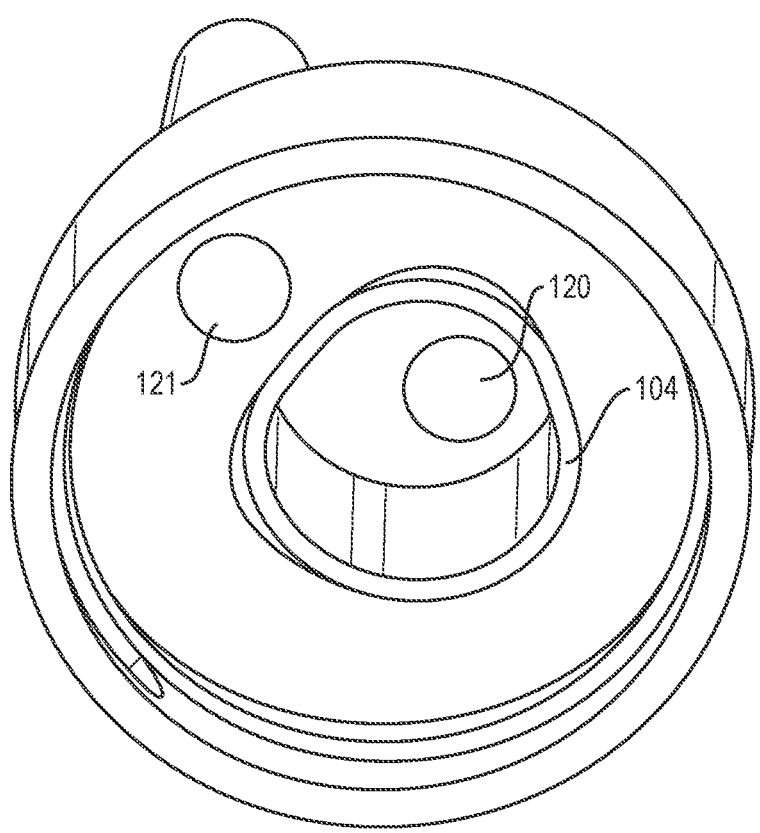
FIG. 4 is an isometric view of the cap of the integrated suction canister of specimen collection device shown with a flexible sealing element installed, according to various embodiments.
Figure 5:
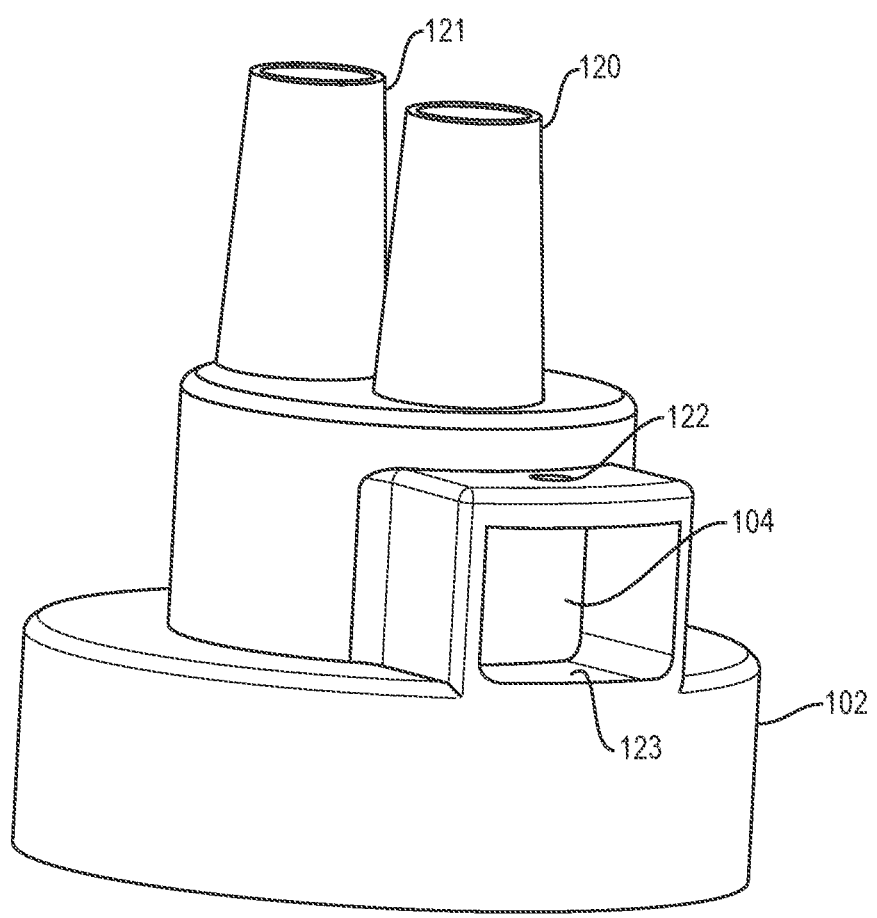
FIG. 5 is a side view of the integrated suction canister of the specimen collection device showing the flexible sealing element blocking the sieve access port, according to various embodiments.
Figure 6:
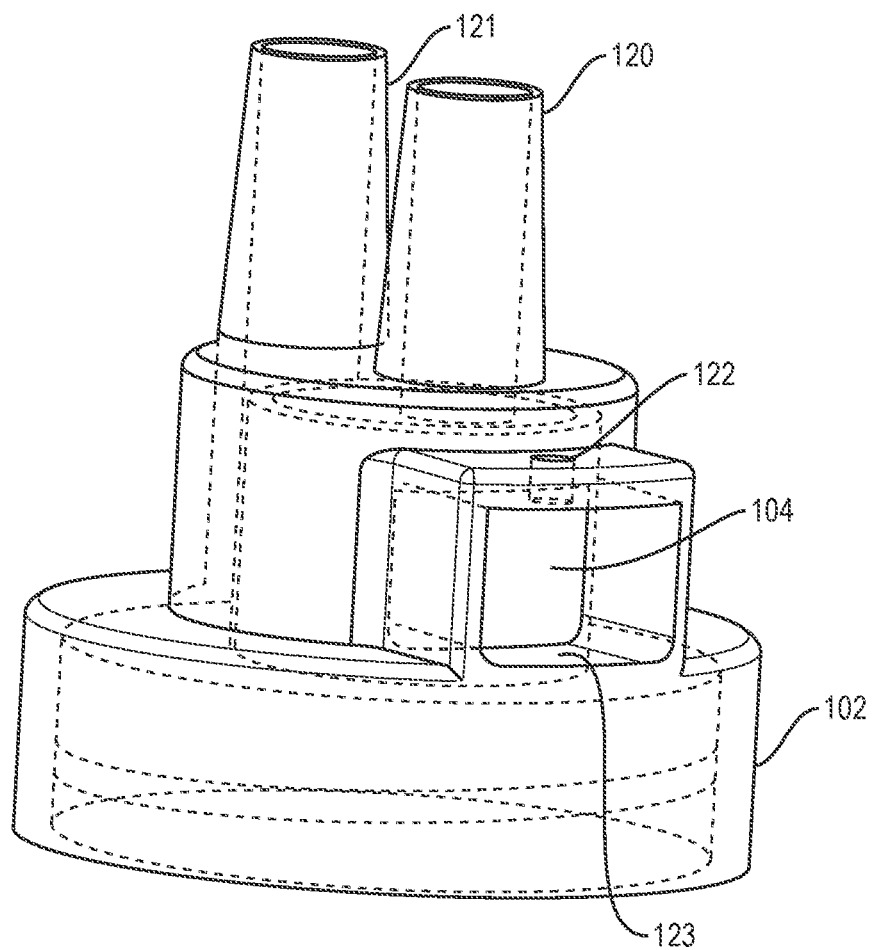
FIG. 6 depicts the same view as in FIG. 5 with the cap viewed in a transparent state to allow clear visualization of sealing element, according to various embodiments.
Figure 7:
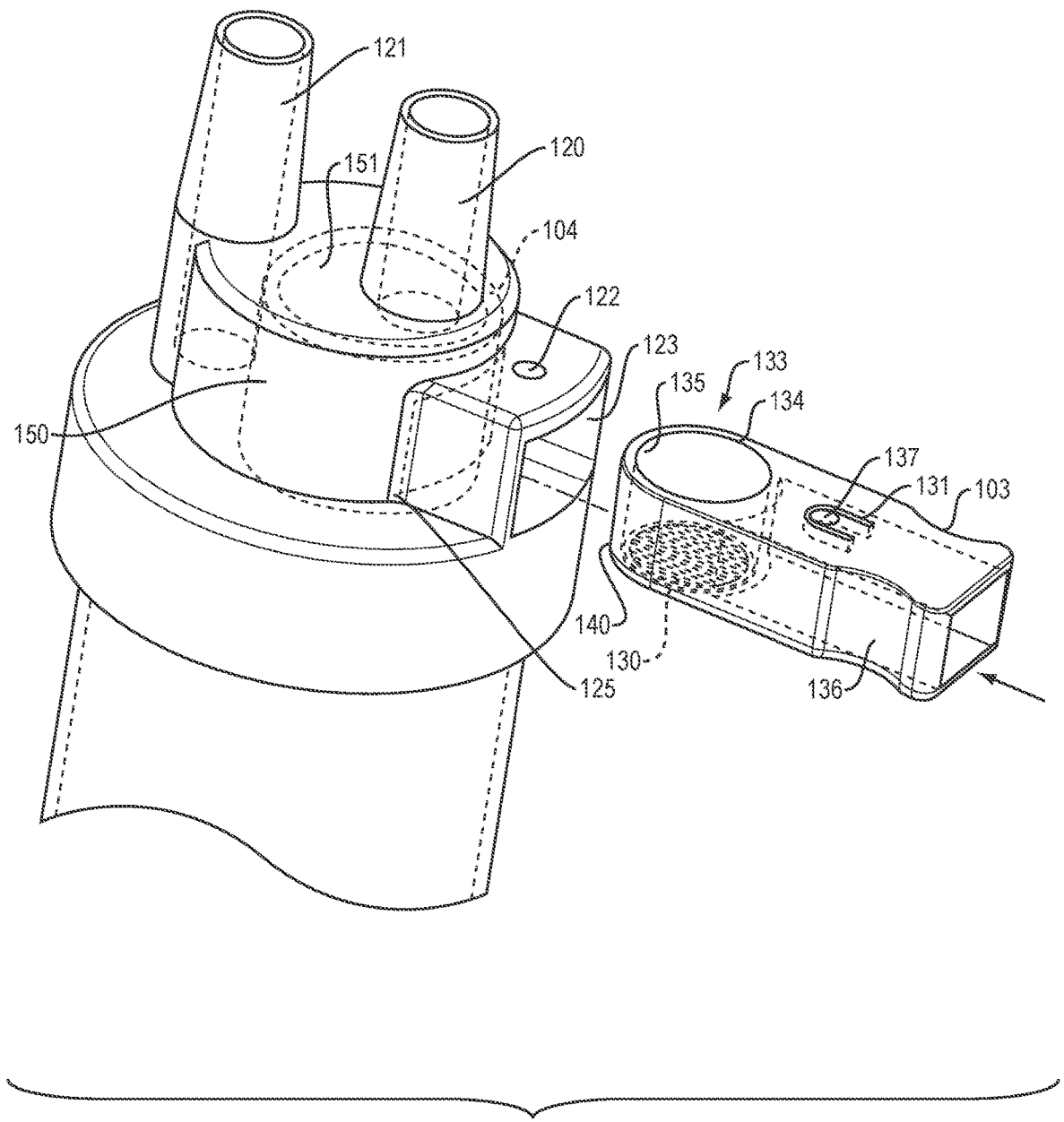
FIG. 7 is a partial isometric view of the integrated suction canister of the specimen collection device with the flexible sealing element in the sealed position, showing the approach of the sieve for installation, according to various embodiments.
Figure 8:
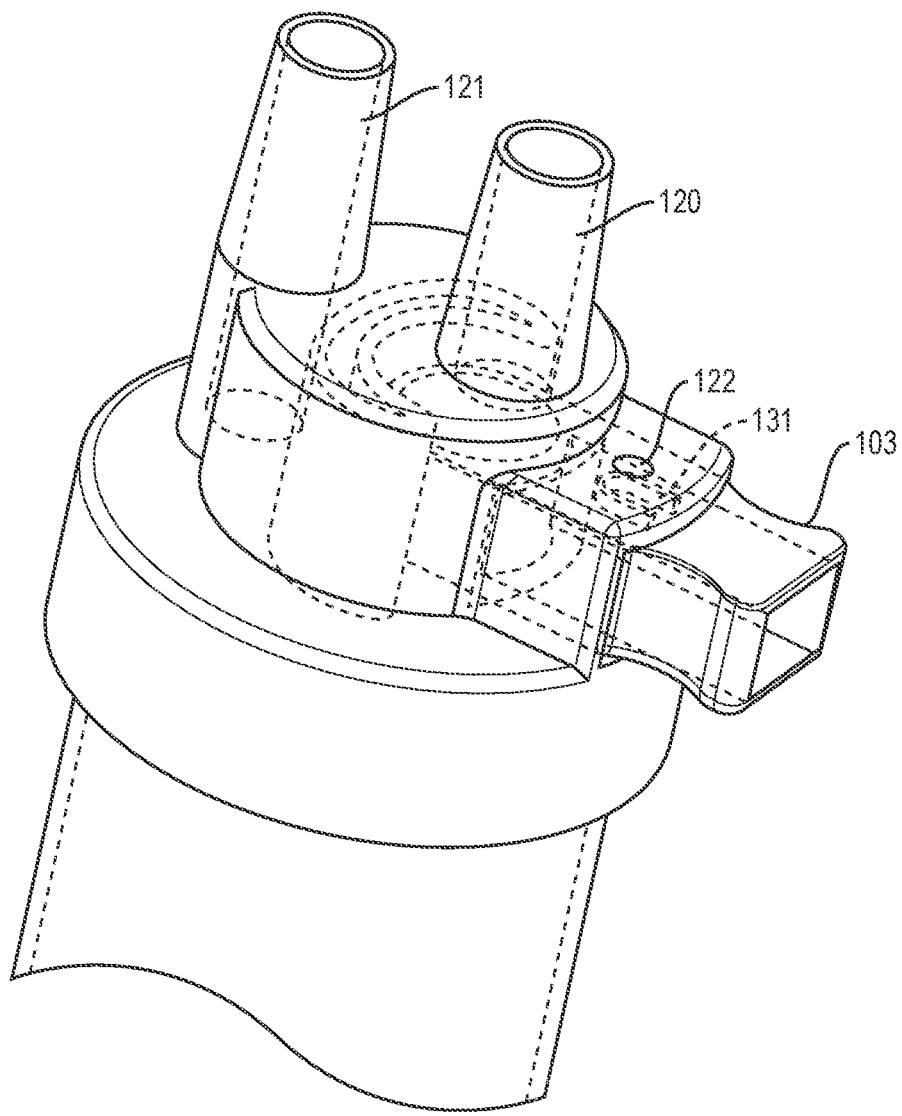
FIG. 8 is a partial isometric view of the integrated suction canister of the specimen collection device with flexible sealing element in the unsealed position after installation of the sieve, according to various embodiments.
Figure 9:
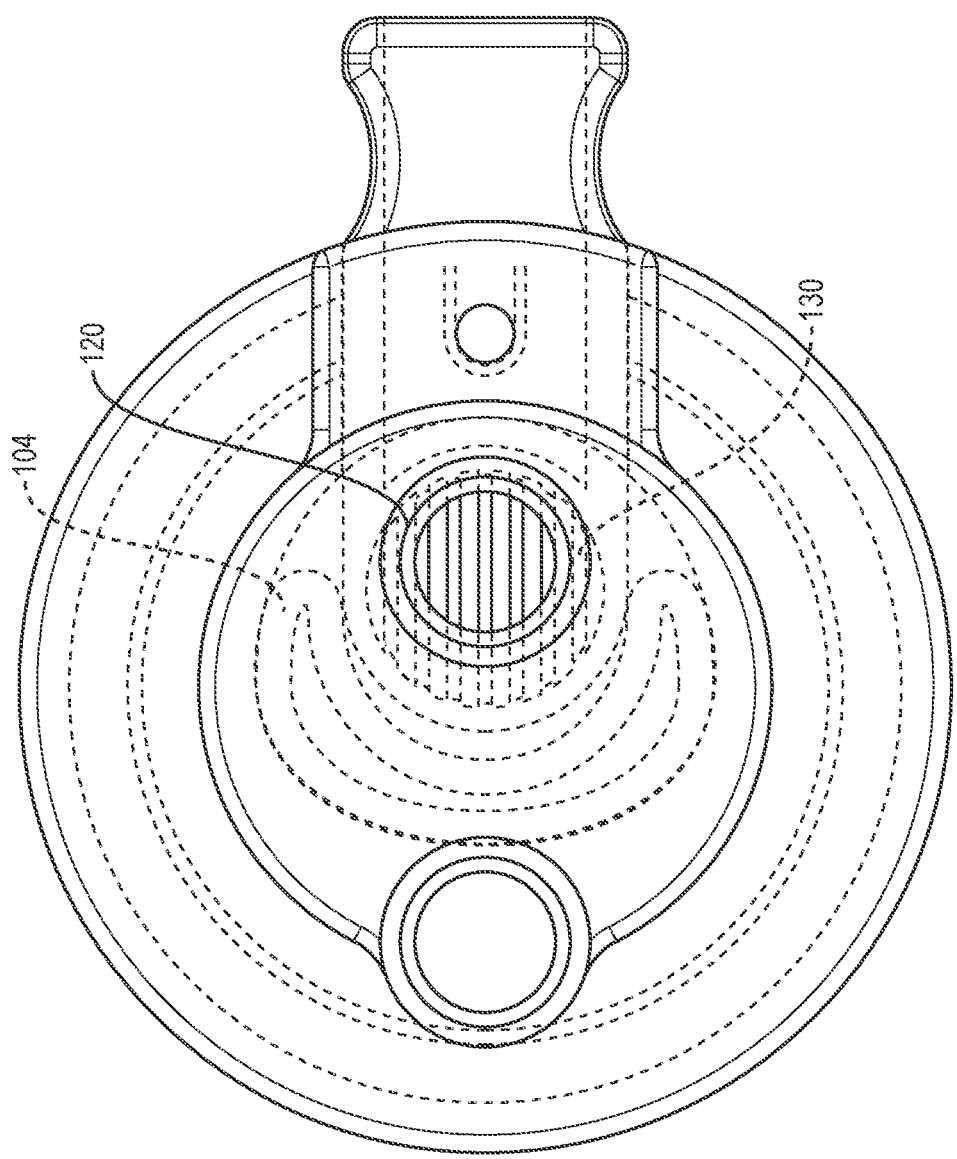
FIG. 9 is a top view of the cap of the integrated suction canister of the specimen collection device shown with flexible sealing element in the unsealed position showing the relationship of the cap inlet port to the seal and sieve, according to various embodiments.

FIG. 2 depicts specimen collection device 100 in an exploded state, also revealing a flexible sealing element 104 not visible in FIG. 1. In general, suction canister lid 102 may be removably coupled to suction canister 101, such as by engaging one or more protrusions on suction canister 101 (e.g., a screw on/off mechanism such as threading, tabs, etc.). Similarly, specimen tray 103 may be removably coupled to suction canister lid 102. When specimen collection device 100 is assembled, flexible sealing element 104, as detailed below, may engage suction canister lid 102 and internal to the assembled specimen collection device 100.

FIGS. 3-10 depicts elements of suction canister lid 102. As shown in the various FIGURES, suction canister lid 102 may generally include an inlet port 120, a suction port 121, a specimen tray access port 123, and a specimen tray retention element/tang detent 122. In use, inlet port 120 is typically connected via a segment of flexible tubing to the outlet of the endoscopic aspiration channel or other suction device being used to remove fluid and biopsied samples from the operative site (not shown). Also during use, suction port 121 is typically connected via a segment of flexible tubing to a suction source (not shown), to provide negative pressure within specimen collection device 100 and draw collected material from the patient into suction canister 101. In some embodiments, a tube may be coupled to the suction canister 101 and to the suction port 121 of the specimen collection device 200. When suction is applied to suction port 121, the suction is directed through the specimen collection device 200, meaning that air, fluid and collected samples are pulled into the collection device 200 via inlet port 120, e.g., using an endoscope.

Suction canister lid 102 may also define a seal cavity 124 into which flexible sealing element 104 may be installed, in various embodiments. The lumen formed by inlet port 120 terminates on the distal face of seal cavity 124 at outlet port 127 such that material passing through inlet port 120 may be free to pass into, and through, seal cavity 124. Specimen tray access port 123 may terminate on the side wall of seal cavity 124 at specimen tray opening 128, providing fluid communication between specimen tray access port 123 and seal cavity 124. The nature of the intersection of access port 123 and the seal cavity 124 is such that a continuous sealing surface 125 on seal cavity 124 extends in an uninterrupted fashion around the entire perimeter of specimen tray opening 128.

FIGS. 4-7 depict various views of suction canister lid 102 with flexible sealing element 104 installed. In various embodiments, flexible sealing element 104 may be an elastomeric component comprising an outer surface 150 and inner bore 151. In this embodiment, flexible sealing element 104 may be elastomeric tubing of a substantially cylindrical shape. Any number of elastomeric materials would be suitable, such as silicone, urethane, or the like. It is essential that the material selected for flexible sealing element 104 be highly resilient such that it will return to its original shape when subjected to deforming loads and subsequently released. In preferred embodiments, the selected material will further be resistant to creep such that if displaced for extended periods of time, the force with which it returns to its original shape is not significantly diminished.

Seal cavity 124 is provided with geometry such that when flexible sealing element 104 is pressed into seal cavity 124, seal cavity 124 presses against flexible sealing element 104, biasing flexible sealing element 104 in the direction of access port 123 and compelling outer surface 150 of flexible sealing element 104 to press firmly against sealing surface 125. In this manner, fluid communication between access port 123 and seal cavity 124 is cut off when flexible sealing element 104 is installed. Likewise, with flexible sealing element 104 so installed, outlet port 127 lies within inner bore 151 of flexible sealing element 104 such that material entering into specimen collection device 100 is free to pass through bore 151 of flexible sealing element 104 into suction canister 101.

Biasing of flexible sealing element 104 further serves to retain flexible sealing element 104 in position such that no further retention components or features are required. However, as would be appreciated, other embodiments might employ such features/components.

Suction port 121 terminates at its distal end at outlet port opening 126. Outlet port opening 126 is positioned such that outlet port opening 126 is in direct fluid communication with the inside of suction canister 101, yet outside of the perimeter of seal cavity 124. In this fashion, materials that enter into specimen collection device 100 through inlet port 120 must first pass through suction canister 101 before passing into suction port 121. In typical use, specimen collection device 100 will be positioned in a generally vertical orientation such that canister 101 is pointed substantially downward. Suction forces conveying material into specimen collection device 100 dissipate significantly when the collected material passes from the comparatively small bore of the inlet tube to the comparatively large bore of suction canister 101. This causes the forces of gravity to overwhelm the suction conveying forces and causes the material to drop to the bottom of suction canister 101. In this fashion, material aspirated into the specimen collection device 100 will collect in suction canister 101 and not pass out of the device 100.

Specimen collection device 100 is further provided with specimen tray 103 for occasions when it is desired to retrieve a biopsied sample for further examination. In one embodiment, specimen tray 103 includes sample cavity 133 disposed at its distal end. Sample cavity 133 is defined by inlet 134, outlet sieve 130, and wall 135. Inlet 134 is fully open so as to allow free passage of aspirated material into sample cavity 133. In various embodiments, outlet sieve 130 may define one or more apertures (e.g., slits, holes of any number of shapes, etc.) such that liquids are free to pass through the openings between the apertures, while solids larger than the opening between the apertures are retained within the cavity defined by wall 135. It is further understood that the size of the openings in outlet sieve 130 can be specified in accordance with the minimum desired sample size that is wished to be retained.

Specimen tray 103 may be configured with tactile (finger) grips 136 to facilitate introduction and retrieval of specimen tray 103 from the suction canister lid 102. Tactile grips 136 are positioned such that they never pass into the suction path. In this fashion, there is minimal opportunity for the tactile grips 136 to become contaminated with aspirated materials. Specimen tray 103 may be further configured with retention feature 131. The purpose of retention feature 131 is to hold specimen tray 103 in position when specimen tray 103 is installed in suction canister lid 102. It is a further function of retention feature 131 to provide tactile feedback to the user when specimen tray 103 has been fully installed. In this embodiment, retention feature 131 is comprised of a deflectable tang configured with a raised bump 137 at its distal end.

As depicted in FIGS. 7-10, specimen tray 103 is installed into the suction canister lid 102 by pushing it into access port 123. When tray distal wall 140 encounters flexible sealing element 104, specimen tray 103 deforms and displaces flexible sealing element 104, lifting flexible sealing element 104 off sealing surface 125 and everting flexible sealing element 104 in on itself. In the fully installed position, outlet port 127 is fully within the opening of sample tray inlet 134. In this manner, any material entering into the specimen collection device inlet must pass through the tray outlet sieve 130 before passing into the suction canister 101. The clearance between outer surfaces of specimen tray 103 and inner surfaces of access port 123 may be very small such that suction leakage through the resulting gaps is minimized and overall suction performance of the system compromised. Alternately, these surfaces may be configured as matched tapers such that they intimately mate when specimen tray 103 is fully installed in the access port 123.

As specimen tray 103 is installed into access port 123, retention tang bump 137 is deflected downward the top surface of access port 123. Retention tang detent 122 is provided on access port 123 and positioned such that when specimen tray 103 is fully installed, retention tang bump 137 is free to snap back to its original position. This snapping action provides tactile feedback to the user that specimen tray 103 has been fully seated.

In addition, when specimen tray 103 in its fully installed position, the resilient nature of flexible sealing element 104 will apply an axial load towards specimen tray 103 that attempts to drive specimen tray 103 out of suction canister lid 102. It is a further function of the retention tang of retention feature 131 in this embodiment to provide resistance to this driving force. Interference and dimensioning of the tang of retention feature 131, retention tang bump 137, and retention tang detent 122 are selected to ensure that displacement forces greater than those created by the seal are required to unseat specimen tray 103.

When the desired sample has been collected in specimen tray 103, the user can grasp tactile grips 136 on specimen tray 103 and withdraw specimen tray 103 and the collected specimen from access port 123. As specimen tray 103 is withdrawn, flexible sealing element 104 will recover to its original position, sealing off access port 123.

Figure 10:
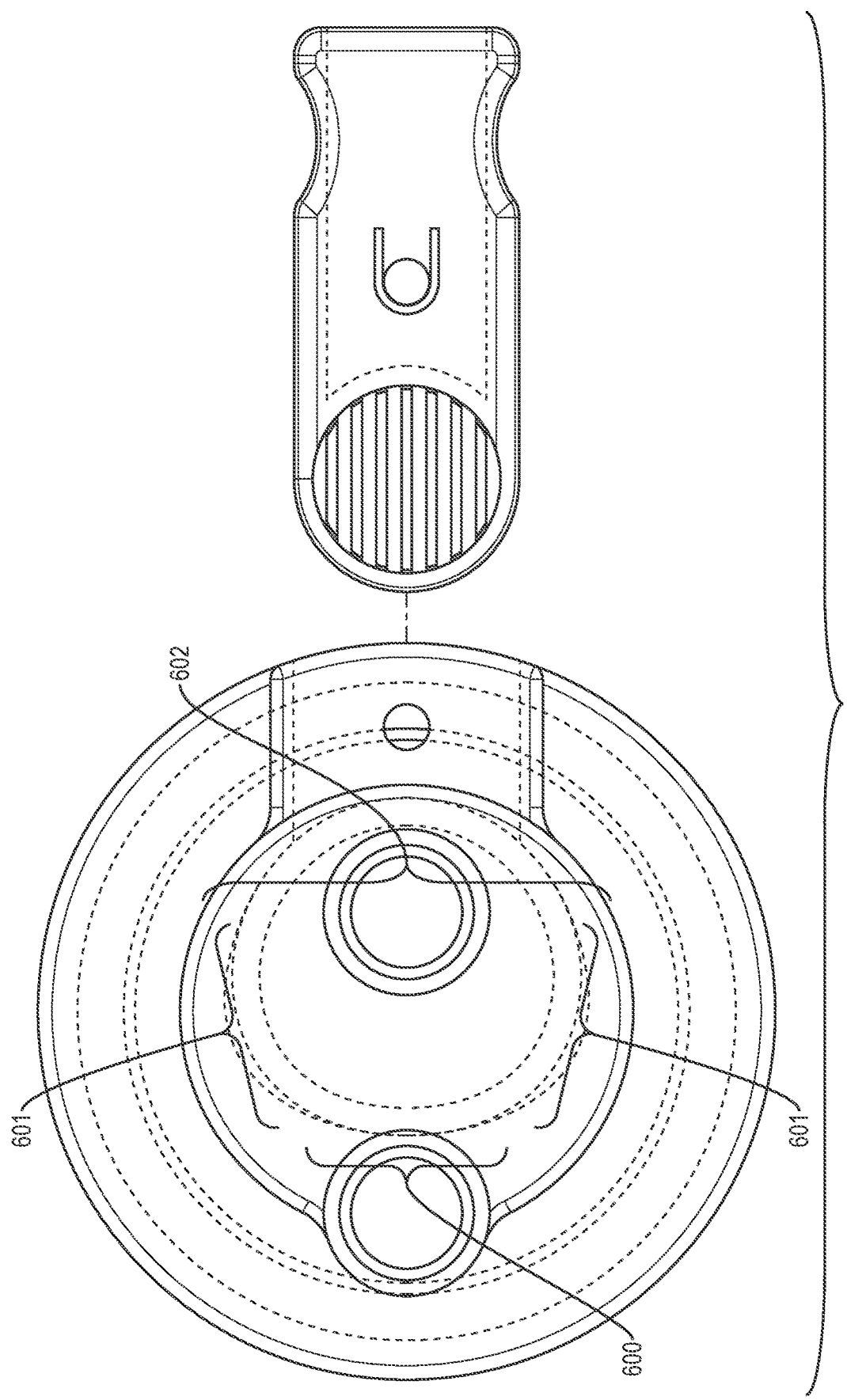
FIG. 10 is a top view of the cap of the integrated suction canister of the specimen collection device shown with flexible sealing element in the sealed position showing the relationship of the cap inlet port to the seal, according to various embodiments.

Referring to FIG. 10, in the described embodiment, the shape of seal cavity 124 is not uniformly round, but rather divided into three discreet zones. Zone 602 is provided for sealing off tray access port 123. This segment is of uniform radius selected to match the outer radius of flexible sealing element 104. Zone 600 is provided to bias seal 104 up against sealing surface 125. This zone comprises a flattened curve such that a cord projected across the midline of the cavity is smaller than the unrestrained diameter of flexible sealing element 104. This causes the seal to be compressed against sealing surface 125. Zone 601 is provided space for deformation of flexible sealing element 104 when specimen tray 103 is installed and does not inhibit recovery of flexible sealing element 104 to its "sealed" position upon removal of specimen tray 103. Zone 601 around the opening of the specimen tray 103 may be "raised" such that sealing forces can be concentrated where the forces are needed, e.g., "relief" is provided in zone 601.

It is common clinical practice that tissue samples retrieved for pathological analysis are transferred to small jars of preserving solutions, such as Formalin. Specimen tray 103 has been designed such that it completely fits within standard sized Formalin jars. Thus it is possible that when a specimen tray 103 is employed to retrieve a specimen, the user can remove specimen tray 103 and drop the entire specimen tray 103 and specimen into the formalin jar without having to remove the specimen from specimen tray 103, eliminating the need to pick out the sample with tweezers, or dumping the contents onto a work surface, providing improved sanitation of the specimen transfer process.

Figure 11:
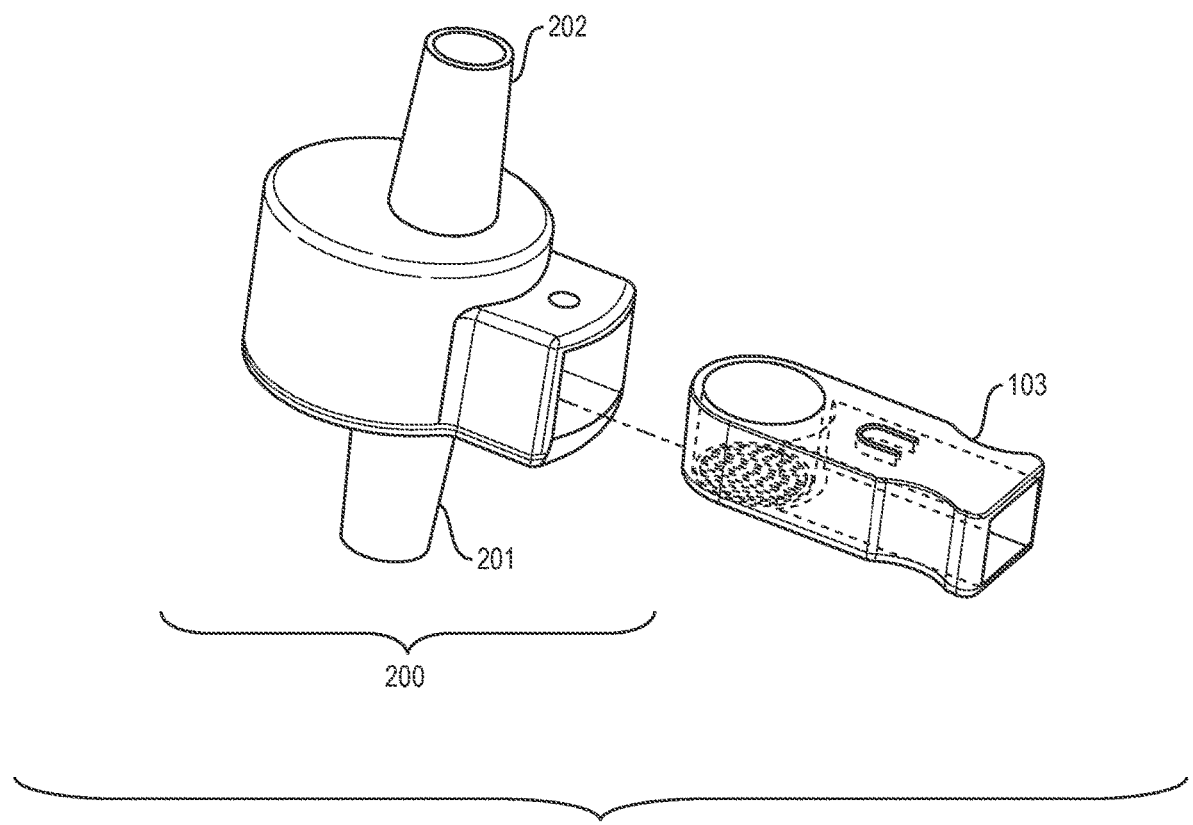
FIG. 11 is an isometric view of an alternate embodiment of the specimen collection device that does not include a suction canister, according to various embodiments.
Figure 12:
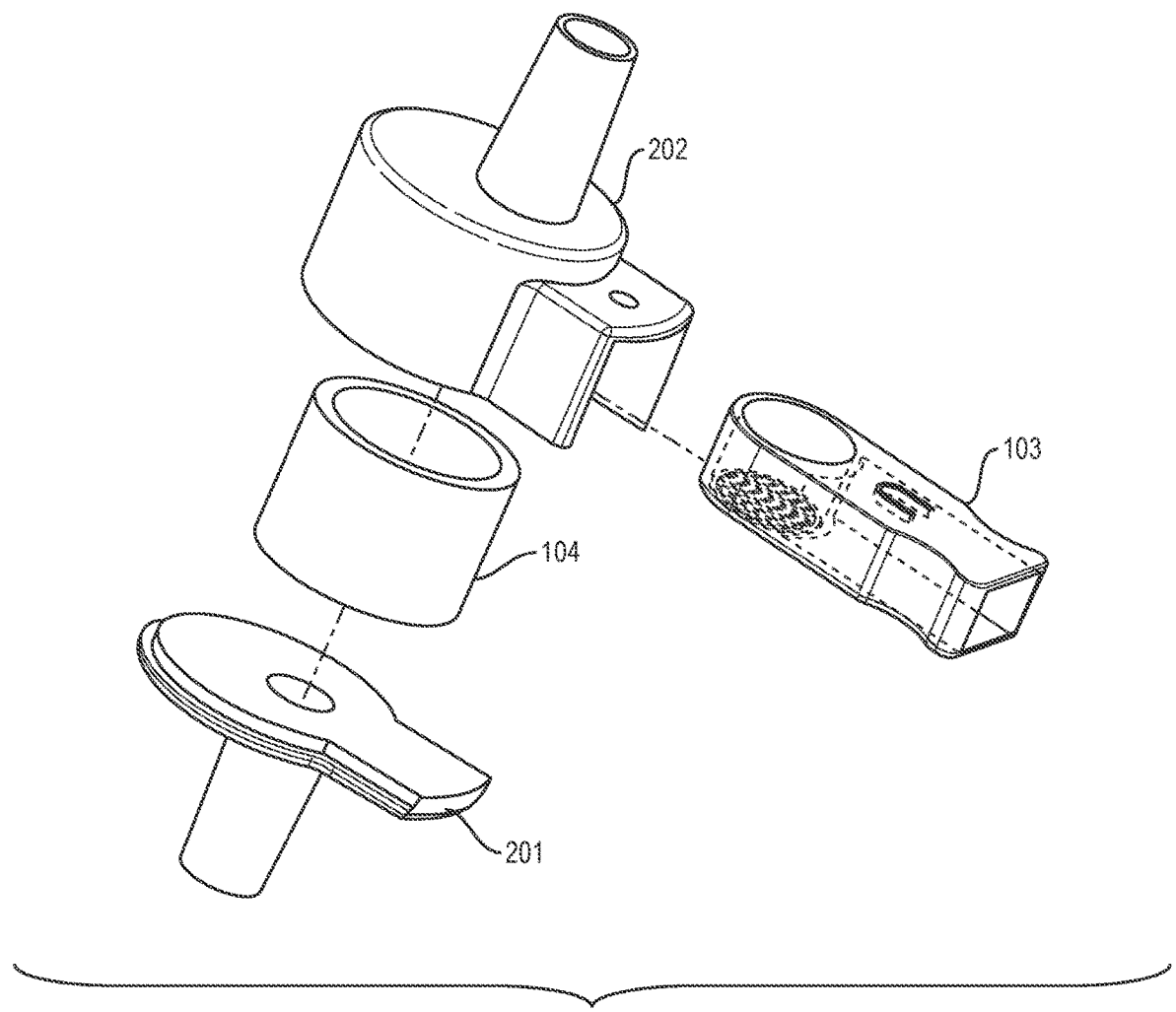
FIG. 12 is an exploded view of the specimen collection device of FIG. 11, according to various embodiments.

An alternate embodiment of a specimen collection device is depicted in FIGS. 11-19. As shown in FIGS. 11-12, specimen collection device 200 is disclosed in recognition of the fact that in many diagnostic or screening procedures, it is not guaranteed that specimen retrieval will be necessary. In these cases, the cost associated with providing specimen retrieval capability may not be warranted. If, however, a suspicious lesion was found and a biopsy performed, the clinician may wish to add a specimen retrieval device. Given that a standard suction canister would typically already be employed in the procedure to allow collection fluid introduced to allow clear viewing of the operative field, it would be faster and more convenient to simply add the specimen retrieval functionality.

Figure 13:
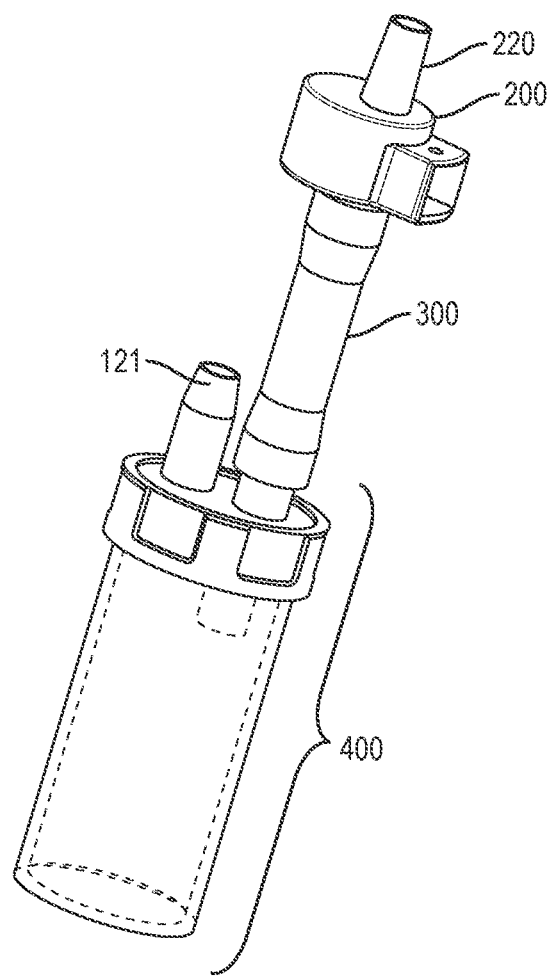
FIG. 13 is an isometric view of the specimen collection device of FIG. 11 showing its use in conjunction with a standard suction canister, according to various embodiments.
Figure 14:
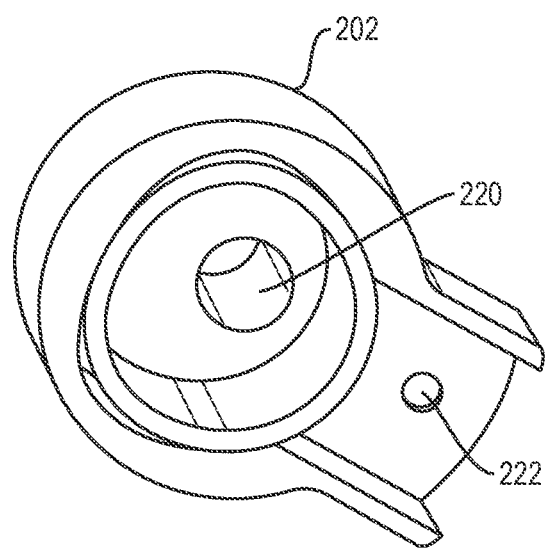
FIG. 14 is an isometric view of the top of the specimen collection device of FIG. 11 shown with flexible sealing element installed, according to various embodiments.
Figure 15:
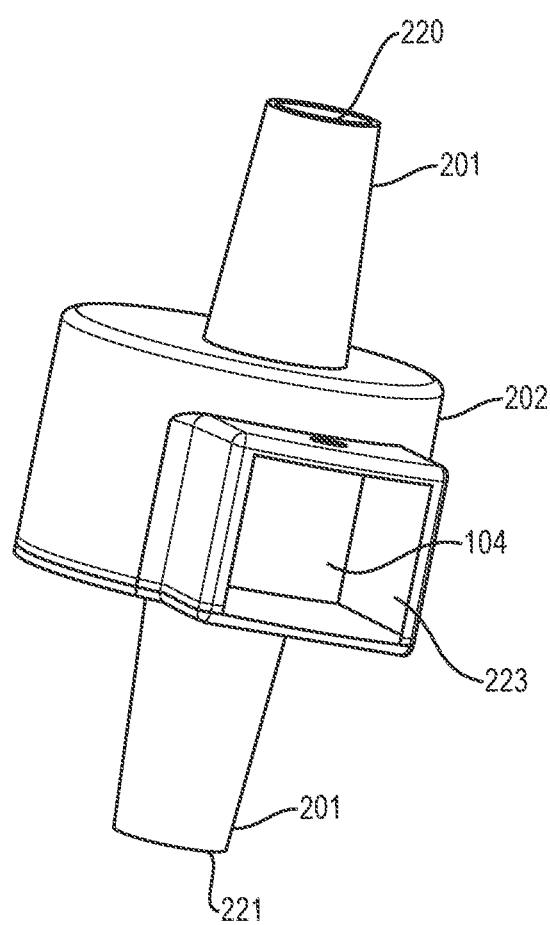
FIG. 15 is a side view of the specimen collection device of FIG. 11 showing the flexible sealing element blocking the sieve access port, according to various embodiments.
Figure 16:
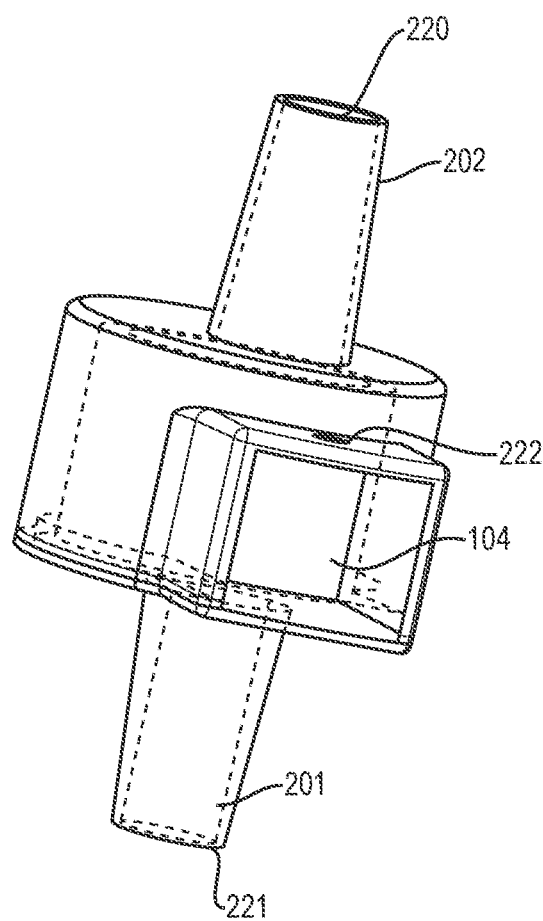
FIG. 16 depicts the same view as in FIG. 15 with the top viewed in a transparent state to allow clear visualization of sealing element, according to various embodiments.
Figure 17:
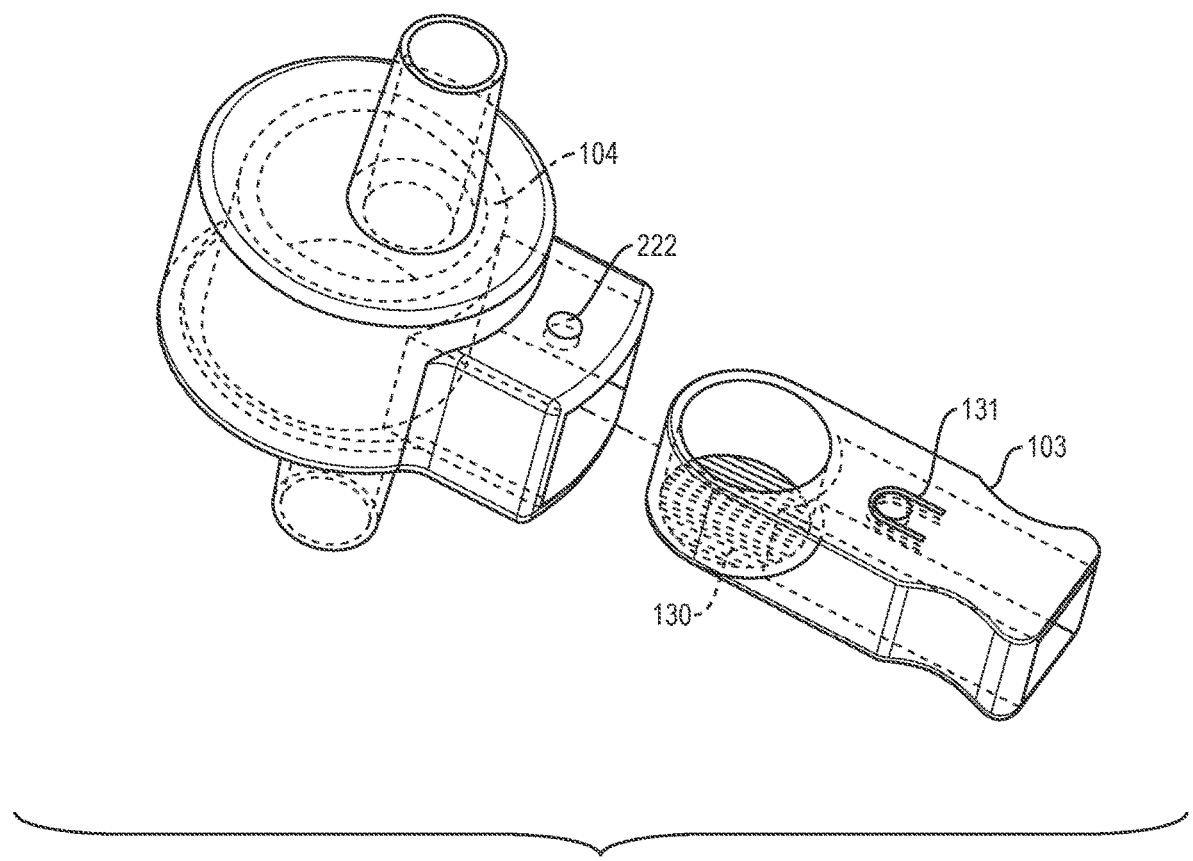
FIG. 17 is a partial isometric view of the specimen collection device of FIG. 11 with flexible sealing element in the sealed position, showing the approach of the sieve for installation, according to various embodiments.
Figure 18:
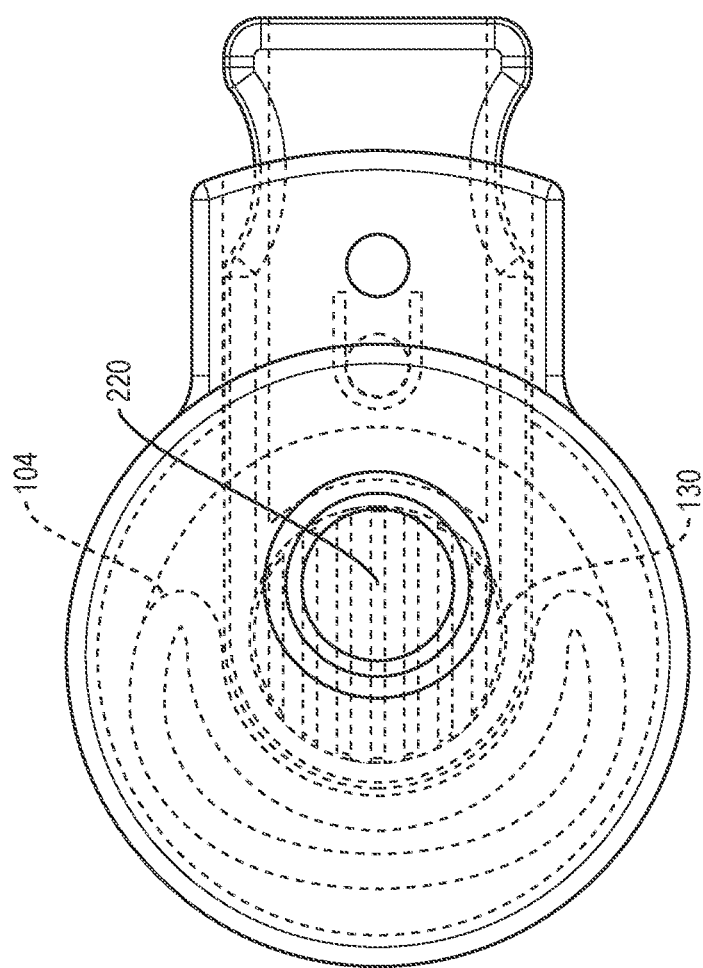
FIG. 18 is a top view of the top of the specimen collection device of FIG. 11 shown with flexible sealing element in the unsealed position showing the relationship of the cap inlet port to the seal and sieve, according to various embodiments.
Figure 19:
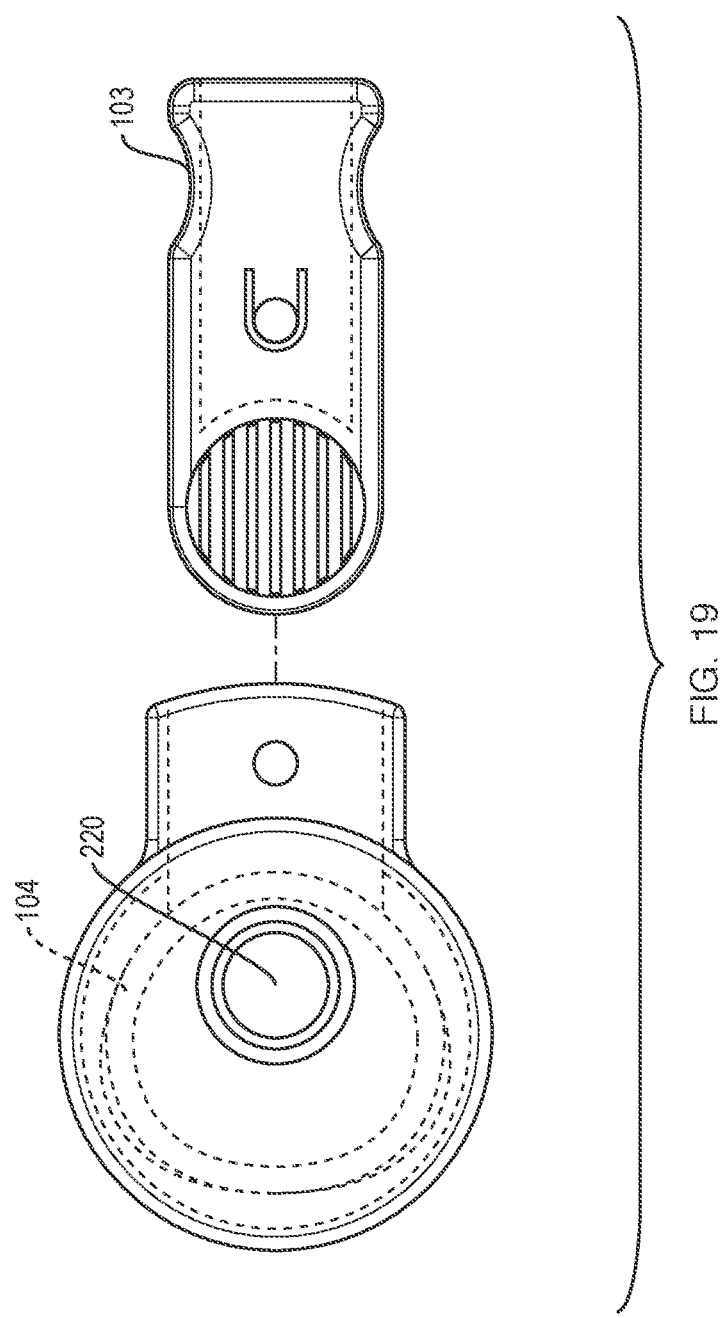
FIG. 19 is a top view of the top of the specimen collection device of FIG. 11 shown with flexible sealing element in the sealed position showing the relationship of the cap inlet port to the seal, according to various embodiments.

FIG. 13 shows the specimen collection device 200 as it would be configured with a standard suction canister, comprising a standard suction canister 400 coupled to the outlet of specimen collection device 200 via tubing 300. Specimen collection device inlet port 220 is connected via a segment of flexible tubing to the outlet of the endoscopic aspiration channel or suction device being used to remove fluid and biopsied samples from the operative site (not depicted).

FIGS. 14-19 illustrate various views of specimen collection device 200. In general, specimen collection device 200 operates in a similar manner as that of specimen collection device 100 described previously. Notably, specimen collection device 200 may define an access port 223 into which specimen tray 103 may be removably coupled. An internal surface of access port 223 may define a retention tang detent 222 into which bump 137 on the tang of retention feature 131 may couple, thereby locking specimen tray 103 into place. Also as shown, particularly in FIG. 18, insertion of specimen tray 103 into specimen collection device 200 will deform flexible sealing element 104 located internal to specimen collection device 200 between inlet port 220 and outlet port 221. In doing so, the apertures (e.g., slits, holes, etc.) of specimen tray 103 are located within the suction pathway, allowing collected fluids to pass through specimen collection device 200 while retaining the solid or semi-solid collected material. As in specimen collection device 100, removal of specimen tray 103 from specimen collection device 200 will cause flexible sealing element 104 to return to its original shape, thereby sealing off access port 223.

Figure 20:
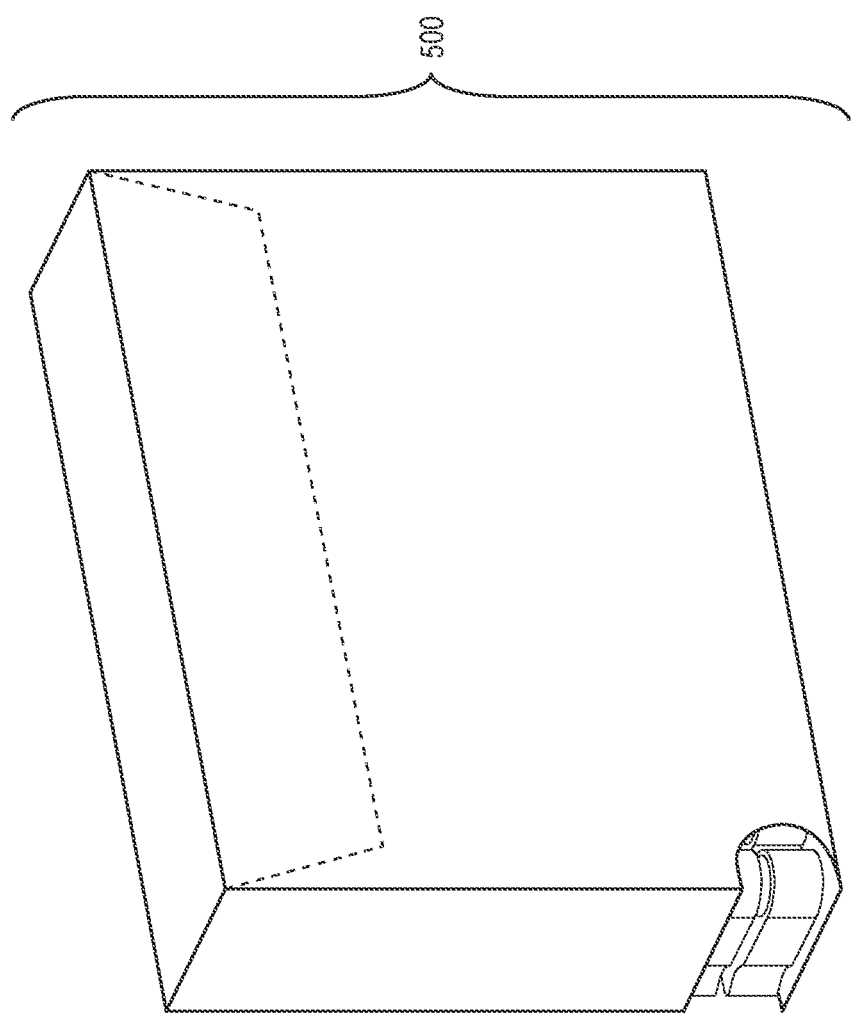
FIG. 20 is an isometric view of a carton for dispensing single units of the sieve, according to various embodiments.
Figure 21:
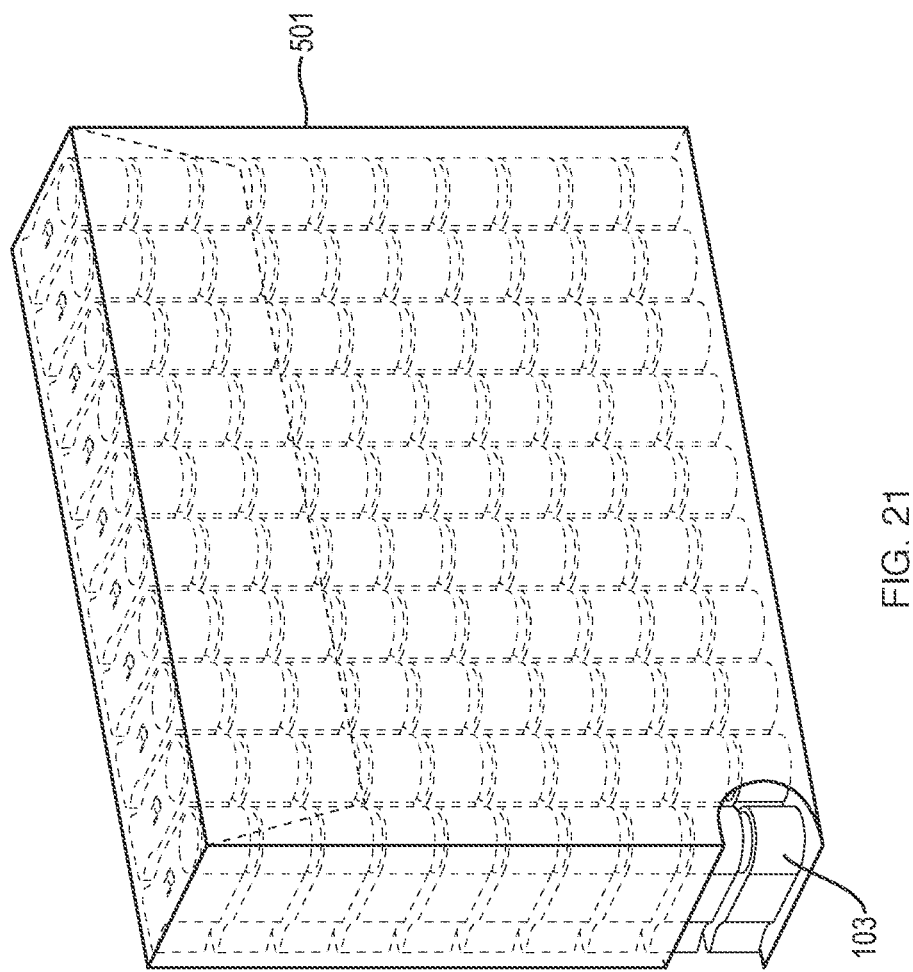
FIG. 21 depicts the same view as in FIG. 20 with the carton being depicted transparent to allow visualization of the contents of the carton, according to various embodiments.

FIGS. 20-21 illustrate an example dispensing carton 500 for a plurality of specimen trays 103, according to various embodiments. In particular, carton 500 may define an inner chamber 501 configured to store an m-by-n number of specimen trays 103 and dispense an individual tray 103, as desired. During use, this addresses the uncertainty of the clinician with respect to the number of specimen trays 103 needed for the endoscopic procedure, as carton 500 provides a large reserve of specimen trays 103 and in an easily retrievable manner. This also enables efficient transfer of each specimen tray 103 into a Formalin jar directly after collection of each specimen and replace that tray with another from carton 500.

FIGS. 22-25 illustrate an additional embodiment of a specimen collection device. In the embodiments shown above, the flexible sealing element may take the form of a substantially cylindrical shape that becomes deformed via insertion of the specimen tray into the access port. In further embodiments, as shown in FIGS. 22-25, the flexible sealing element may, instead, be arc-shaped (e.g., not a full cylinder). In addition, the internal structures of the specimen collection device may be configured to retain and support the arc-shaped flexible sealing element when sealing the access port and when the element is deformed by insertion of the specimen tray. Preliminary testing has shown this approach to provide improved performance with less sensitivity to dimensional tolerances.

Figure 22:
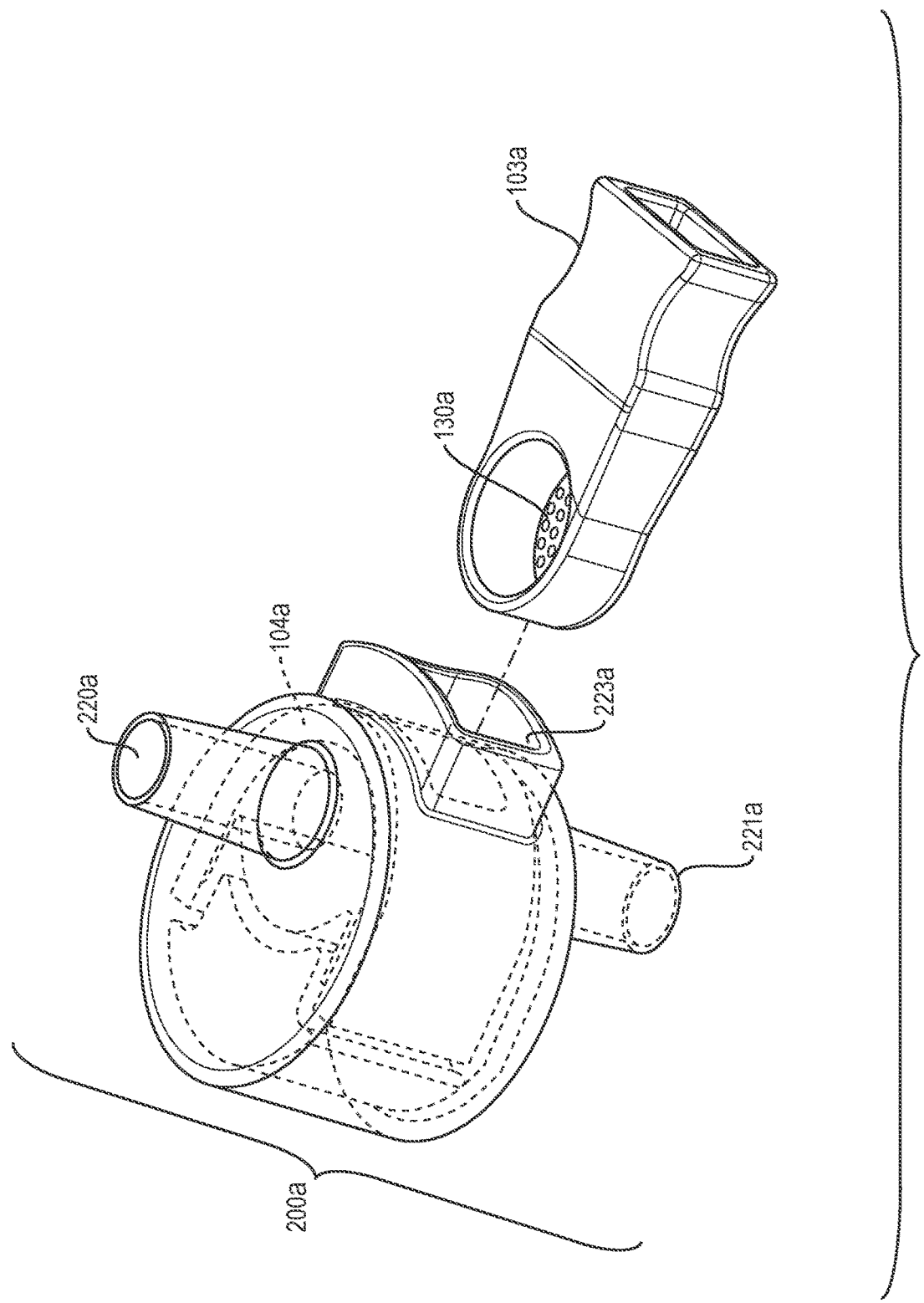
FIG. 22 is an isometric view of the specimen collection device, according to various embodiments.

FIG. 22 is an isometric view of the specimen collection device 200a, according to various embodiments. The specimen collection device 200a includes inlet port 220a, a flexible sealing element 104a, an access port 223a, and an outlet port 221a. The specimen tray 103a includes outlet sieve 130a, wherein the outlet sieve of the specimen tray 103a is disposed within a sample cavity located at an end of the specimen tray 103a.

As shown in FIG. 22, the inlet port 220a and the outlet port 221a are on opposing ends of the specimen collection device 200a. The inlet port 220a and the outlet port 221a define an aperture that extends through the specimen collection device 200a. During use, the inlet port 220a of the specimen collection device 200a may be coupled to an endoscope, laparoscope, or other medical instrument.

The access port 223a, as illustrated, is substantially perpendicular to the aperture defined by the inlet port 220a and the outlet port 221a. The access port 223a is configured to receive the specimen tray 103a with the outlet sieve 130a.

The flexible sealing element 104a, as illustrated in FIG. 22, is of a substantially curved shape that is located at a first position within the specimen collection device 200a between the aperture and the access port 223a, such that the access port 223a is sealed when the specimen tray 103a is not inserted into the access port 223a.

Figure 23:
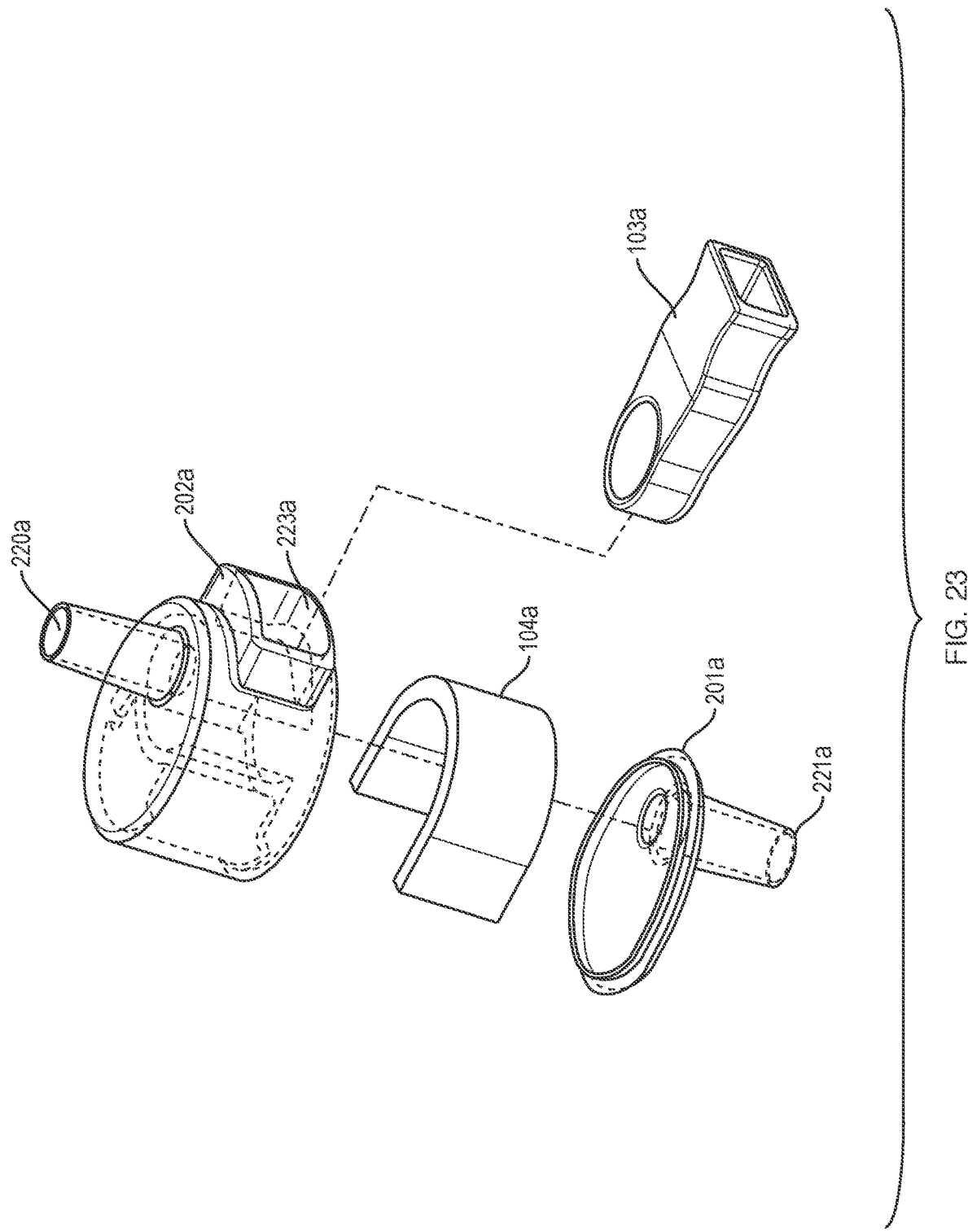
FIG. 23 is an exploded view of the specimen collection device and a side view of the specimen tray, according to various embodiments.

FIG. 23 is an exploded view of the specimen collection device and a side view of the specimen tray, according to various embodiments. As shown in FIG. 23, specimen collection device 200a includes a lower portion 201a and an upper portion 202a. As shown in FIG. 23, the one-piece configuration includes an upper portion 202a coupled to a lower portion 201a to retain flexible sealing element 104a within specimen collection device 200a. In another embodiment, the specimen collection device 200a is configured as a two-piece construction, instead of the one-piece construction shown in FIG. 23.

Figure 24:
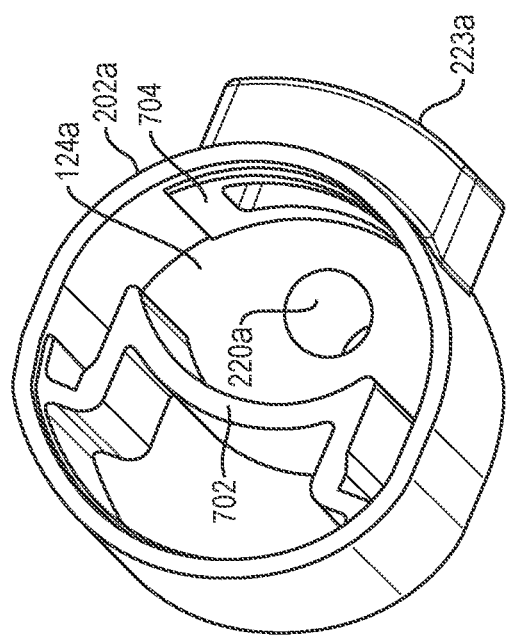
FIG. 24 is a side view of the sealing element retaining wall of the specimen collection device, according to various embodiments.

FIG. 24 is a side view of the sealing element retaining wall 702 of the specimen collection device 200a, according to various embodiments. As shown in FIG. 24, sealing element retaining wall 702 is on an opposing side of the aperture formed by the inlet port 220a and outlet port 221a as that of the access port 223a and its opening 704 and provides a semi-circle around the seal cavity 124a, and inlet port 220a. Sealing element retaining wall 702 provides a force to the flexible sealing element 104a (shown in FIGS. 22 and 23) that is opposite the insertion force when the specimen tray 103a is inserted into the access port 223a, thereby causing the flexible sealing member 104a to deform when the specimen tray 103a is inserted into the access port 223a. In some embodiments, the flexible sealing element 104a is arc-shaped when located in the first position and contacts the sealing element retaining wall 702 at one or more locations along the sealing element retaining wall 702. As illustrated in FIG. 24, the arc-shaped sealing element retaining wall 702 provides a baffle to direct air flow through the outlet sieve of the specimen tray 103 when inserted.

Figure 25:
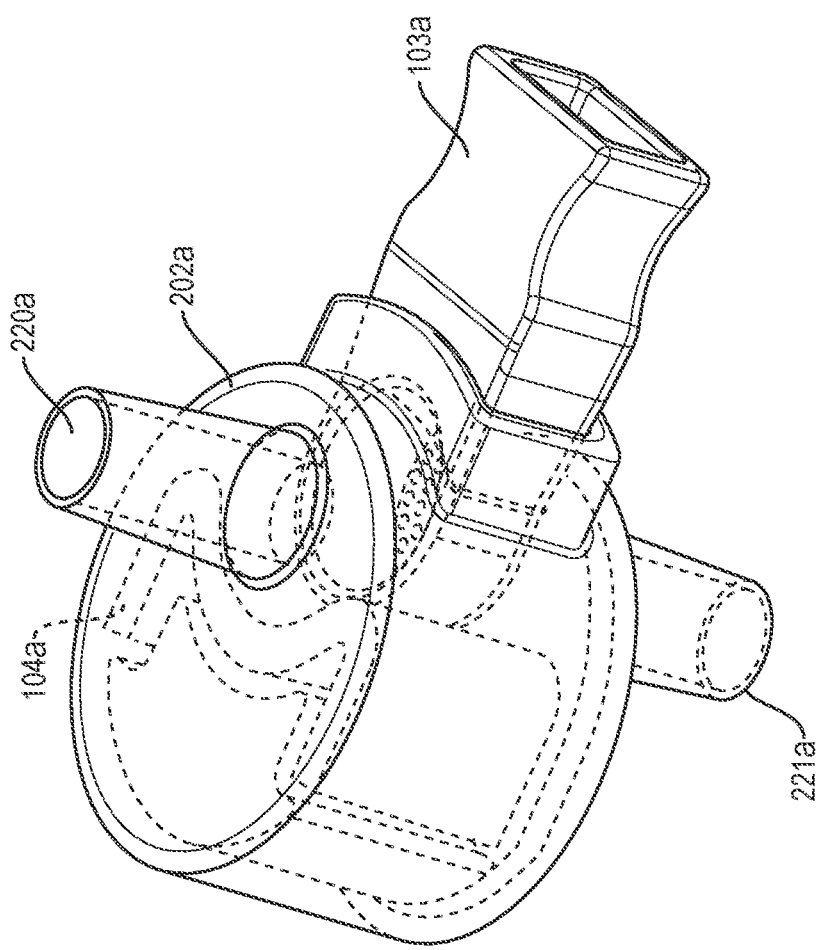
FIG. 25 is a partial isometric view of the specimen collection device with flexible sealing element in the unsealed position after installation of the specimen tray, according to various embodiments.

FIG. 25 is a partial isometric view of the specimen collection device 200a with flexible sealing element 104a in the unsealed position after installation of the specimen tray 103a, according to various embodiments. As shown in FIG. 25, specimen collection device 200a receives the specimen tray 103a such that the outlet sieve 130a of the specimen tray 103a is aligned with the aperture when the specimen tray 103a is fully inserted into the access port 223a. The flexible sealing element 104a deforms in response to an insertion force applied to the specimen tray 103a to insert the specimen tray 103a into the access port 223a, and is located at a second position, as shown in FIG. 25, that is on an opposing side of the aperture as that of the first position, illustrated by FIG. 22, when the specimen tray 103a is fully inserted into the access port 223a.

As illustrated in FIG. 25, there is an aperture extending from inlet port 220a through outlet port 221a. At a first position, the flexible sealing element 104a is located at a first position within the specimen collection device between the aperture and the access port 223a, such that the access port 223a is sealed when the specimen tray 103a is not inserted into the access port 223a. As the specimen tray 103a is fully inserted into access port 223a via an applied insertion force, the flexible sealing element 104a deforms to a second position on an opposing side of the aperture as that of the first position. In the second position, suction is applied through the inlet 220a and outlet ports 221a and the outlet sieve of the specimen tray 103a to receive one or more specimens within the outlet sieve 130a of the specimen tray 103a.

Figure 26:
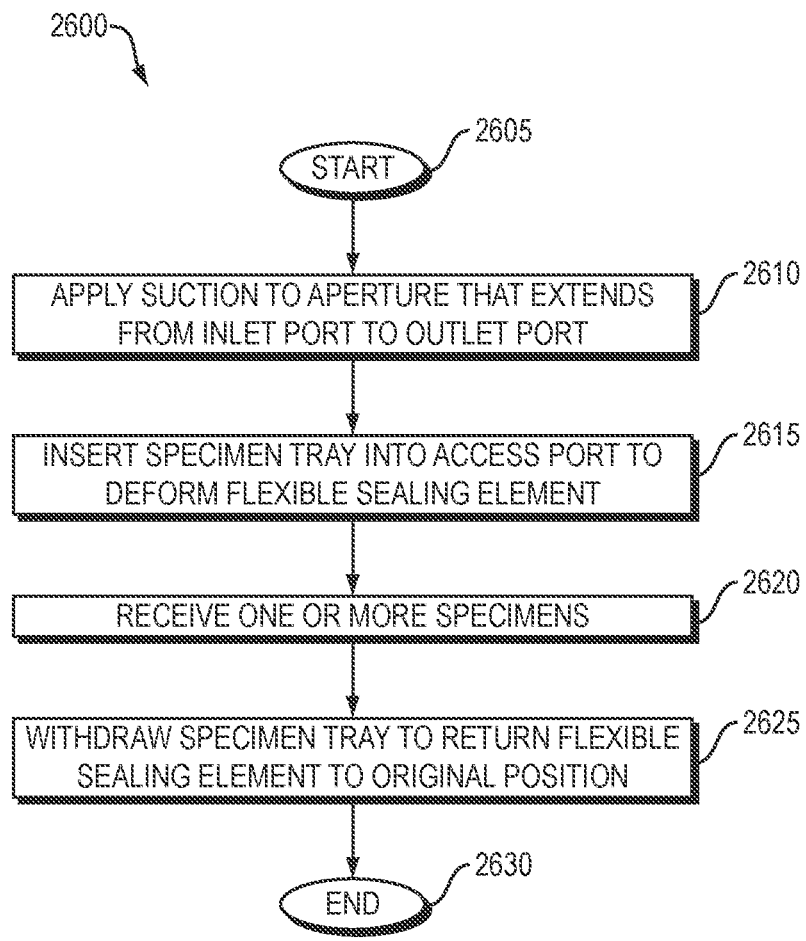
FIG. 26 illustrates a simplified procedure for using a specimen collection device, according to various embodiments.

FIG. 26 illustrates a simplified procedure of using a specimen collection device, according to various embodiments described herein. Procedure 2600 may start at step 2605 and continue to step 2610, where, as described in greater detail above, suction is applied to an aperture defined by the specimen collection device that extends from an inlet port of the specimen collection device to an outlet port of the specimen collection device. In some embodiments, the specimen collection device couples to an endoscope, a laparoscope, or other medical instrument.

In step 2615, as described in greater detail above, the specimen tray is inserted into an access port of the specimen collection device to deform a flexible sealing element of the collection device. The flexible sealing element may be deformed by moving from a first position within the specimen collection device between the aperture and the access port to a second position that is on an opposing side of the aperture as that of the first position when the specimen tray is fully inserted into the access port.

In step 2620, the specimen tray receives one or more specimens. In some embodiments, the procedure may include filtering of a substance containing one or more specimens through an outlet sieve disposed within a sample cavity located at an end of the specimen tray and retaining the one or more specimens within the sample cavity.

In step 2625, as the specimen tray is withdrawn, the flexible sealing element returns to an original position. In some embodiments, as the specimen tray is withdrawn, the flexible sealing element seals off the access port of the specimen collection device. In some embodiments, the specimen tray may be designed for ease of withdrawal. For example, the specimen tray may include tactile grips to improve the withdrawal of the specimen tray from the specimen collection device. These grips may be applied at different locations along the specimen tray depending on the procedure, the user, etc.

The specimen tray may be transferred directly into a container for assessment. In some embodiments, the design of the specimen tray aligns with the container to reduce possible contamination by preventing another step in the process. In other embodiments, the specimen tray includes one or more individual compartments to collect one or more specimens that can be directly transferred for assessment. Procedure 2600 then ends at step 2630.

It should be noted that while certain steps within procedure 2600 may be optional as described above, the steps shown in FIG. 26 are merely examples for illustration, and certain other steps may be included or excluded as desired. Further, while a particular order of the steps is shown, this ordering is merely illustrative, and any suitable arrangement of the steps may be utilized without departing from the scope of the embodiments herein.

Accordingly, the specimen collection devices introduced herein allow a clinician to continue the endoscopic and other medical procedures with minimal interruption while a specimen is removed and deposited in a Formalin container. Notably, with current specimen collection devices, retrieval of the collected specimen requires either disassembling the suction canister or removing a specimen collection sieve. In the former case, the suction canister system is disabled until such time as the sample is collected and the canister re-assembled. In the latter case, the absence of the self-sealing features introduced herein disables the use of the suction canister system until the sieve is replaced.

In further aspects, the specimen collection devices introduced herein allow for the use of the device without the installation of a sieve. In doing so, if the clinician does not encounter a specimen to be collected during the procedure, the additional cost and waste associated with the unused sieve can be avoided.

In addition, the specimen collection devices introduced herein provide a more hygienic process to transfer the collected sample to a Formalin container. When a sample is collected in the sieve, the medical staff can simply pull the sieve from the device and drop the sieve into the formalin vial. As they pull the sieve from the device, the self-sealing aspects of the collection devices introduced herein close the sieve access port, preventing inadvertent spillage of waste/fluid from the suction circuit. By contrast, medical staff using suction canisters must disassemble the canister, and dump the contents of the canister onto gauze, to separate the specimen. As the canister may be filled with body waste and fluids, this can be a particularly unseemly task.

As will be appreciated, the above examples are intended only for the understanding of certain aspects of the techniques herein and are not limiting in nature. While the techniques are described primarily with respect to a particular device or system, the disclosed processes may be executed by other devices according to further implementations. For example, while the techniques herein are described primarily with respect to collection of specimens during endoscopic procedures, the devices and techniques introduced herein are not limited as such and can be adapted for use during other forms of procedures, as well, without undue experimentation.

The foregoing description has been directed to specific embodiments. It will be apparent, however, that other variations and modifications may be made to the described embodiments, with the attainment of some or all of their advantages. Accordingly, this description is to be taken only by way of example and not to otherwise limit the scope of the embodiments herein. Therefore, it is the object of the appended claims to cover all such variations and modifications as come within the true spirit and scope of the embodiments herein.

What is claimed is:

1. A specimen collection device comprising:
    an inlet port and an outlet port on opposing ends of the specimen collection device, wherein the inlet port and the outlet port define an aperture that extends through the specimen collection device,
    an access port located perpendicular to the aperture defined by the inlet port and the outlet port and where the access port is configured to receive a specimen tray having an outlet sieve such that the outlet sieve of the specimen tray is aligned with the aperture when the specimen tray is fully inserted into the access port,
    a flexible sealing element of a curved shape that is located at a first position within the specimen collection device between the aperture and the access port such that the access port is sealed when the specimen tray is not inserted into the access port,
    wherein the sealing element is configured to deform in response to an insertion force applied to the specimen tray to insert the specimen tray into the access port,
    and wherein the sealing element is located at a second position within the specimen collection device that is on an opposing side of the aperture as that of the first position when the specimen tray is fully inserted into the access port;
    and a suction canister, wherein the flexible sealing element is self-sealing within the specimen collection device such that suction is maintained within the specimen collection device regardless of whether the specimen tray is inserted.

2. The specimen collection device of claim 1, further comprising:
    the specimen tray, wherein the outlet sieve of the specimen tray is disposed within a sample cavity located at an end of the specimen tray.

3. The specimen collection device of claim 1, further comprising:
    a suction port.

4. The specimen collection device of claim 1, wherein the flexible sealing element is of a cylindrical shape when the flexible sealing element is located within the specimen collection device at the first position.

5. The specimen collection device of claim 1, wherein specimen collection device further comprises:
    a sealing element retaining wall that provides a force to the flexible sealing element that is opposite that of the insertion force when the specimen tray is inserted into the access port, thereby causing the flexible sealing element to deform when the specimen tray is inserted into the access port.

6. The specimen collection device of claim 5, wherein the flexible sealing element is arc-shaped when located in the first position and contacts one or more locations along the sealing element retaining wall.

7. The specimen collection device of claim 1 wherein the specimen collection device comprises:
    one or more protrusions that directly couple the specimen collection device to the suction canister.

8. The specimen collection device of claim 1, further comprising:
    a tube coupled to the suction canister and to the outlet port of the specimen collection device.

9. The specimen collection device of claim 8, wherein the suction canister further comprises:

a first port to receive the tube for coupling the suction canister to the outlet port of the specimen collection device;

and a suction port.

10. The specimen collection device of claim 1, wherein the specimen collection device is configured to couple with an endoscope.

11. The specimen collection device of claim 1, wherein the specimen tray further comprises:

tactile grips to facilitate retrieval of the specimen tray.

12. A specimen collection device comprising:

means for directing suction through the specimen collection device;

collection means for collecting a specimen within a pathway of the suction;

access means for accepting the collection means into the specimen collection device;

and sealing means for self-sealing the access means from within the specimen collection device such that the suction is maintained through the specimen collection device when the collection means is not inserted into the access means.

13. The specimen collection device of claim 12, wherein the collection means is a first collection means, the specimen collection device further comprising:

second collection means for collecting specimens when the first collection means is not inserted into the access means of the specimen collection device.

* * * * *